(12) United States Patent
Downs

(10) Patent No.: US 6,869,792 B2
(45) Date of Patent: Mar. 22, 2005

(54) METHOD AND APPARATUS FOR PERFORMING MULTIPLE PROCESSING STEPS ON A SAMPLE IN A SINGLE VESSEL

(75) Inventor: Robert Charles Downs, La Jolla, CA (US)

(73) Assignee: IRM, LLC, Hamilton (BM)

( * ) Notice: Subject to any disclaimer, the term of this patent is extended or adjusted under 35 U.S.C. 154(b) by 351 days.

(21) Appl. No.: 09/810,020

(22) Filed: Mar. 16, 2001

(65) Prior Publication Data

US 2002/0132286 A1 Sep. 19, 2002

(51) Int. Cl.[7] ............ C12M 1/00; C12M 3/00; C12N 1/00; C07H 21/04
(52) U.S. Cl. ............ 435/294.1; 435/41; 435/68.1; 435/254.21; 435/295.1; 435/254.1; 536/23.1; 536/23.7; 536/23.74
(58) Field of Search .............. 435/68.1, 98.1, 435/254.1, 254.21, 294.1, 295.1, 41; 536/23.1, 23.7, 23.74

(56) References Cited

U.S. PATENT DOCUMENTS

| | | |
|---|---|---|
| 4,490,436 A | 12/1984 | Kawakami et al. |
| 4,927,545 A | 5/1990 | Roginski |
| 5,114,858 A | 5/1992 | Williams et al. |
| 5,308,506 A | 5/1994 | McEwen et al. |
| 5,330,916 A | 7/1994 | Williams et al. |
| 5,366,896 A | 11/1994 | Margrey et al. |
| 5,578,269 A | 11/1996 | Yaremko et al. |
| 5,620,898 A | 4/1997 | Yaremko et al. |
| 5,622,819 A | 4/1997 | Herman |
| 5,730,697 A | 3/1998 | Auchinleck |
| 5,769,775 A | 6/1998 | Quinlan et al. |
| 5,789,168 A | 8/1998 | Leushner et al. |
| 5,830,657 A | 11/1998 | Leushner et al. |
| 5,902,549 A | 5/1999 | Mimura et al. |
| 5,925,514 A | 7/1999 | Layne et al. |
| 5,968,731 A | 10/1999 | Layne et al. |
| 6,060,022 A | 5/2000 | Pang et al. |
| 6,068,393 A | 5/2000 | Hutchins et al. |
| 6,133,019 A | 10/2000 | Herman |
| 6,162,399 A | 12/2000 | Martinell Gisper-Sauch |
| 6,197,517 B1 | 3/2001 | Roberts |

FOREIGN PATENT DOCUMENTS

WO    WO 97/15588 A1    5/1997

*Primary Examiner*—Jon Weber
*Assistant Examiner*—Kailash C. Srivastava
(74) *Attorney, Agent, or Firm*—Timothy L. Smith; Christopher C. Sappenfield; Quine Intellectual Property Law Group, P.C.

(57) ABSTRACT

A method is provided which comprises: performing a plurality of fermentations, each fermentation in a different sample vessel; and performing a further processing step on the plurality of fermented samples where the sample is retained in the same sample vessel as the fermentation during the processing step.

21 Claims, 8 Drawing Sheets

METHOD AND APPARATUS FOR
PERFORMING MULTIPLE PROCESSING
STEPS ON A SAMPLE IN A SINGLE VESSEL

FIELD OF THE INVENTION

The present invention relates generally to a method and apparatus for performing multiple processing steps on a sample in a single vessel. More specifically, the present invention relates to a method and apparatus useful, for example, in biomedical and biotechnology processes such as an automated centrifugation and fermentation process.

BACKGROUND OF THE INVENTION

Processing of a sample such as a biological sample for fermentation and centrifugation typically requires use of more than one vessel. For example, fermentation is carried out in one vessel and then the sample must be transferred to another vessel before the sample can be placed in a centrifuge for further processing. In addition, such multiple process procedures may require significant manual intervention to transfer the sample from one vessel to another and from one processing device or station to another.

Fermentation is a key technology in many fields and industries and is performed both on a mass production scale and on an experimental, bench top scale. For example, fermentation systems are used for the production of a large number of products such as antibiotics, vaccines, synthetic biopolymers, synthetic amino acids, and proteins. Fermentation technology is integral in the production of recombinant proteins using biological organisms such as E. coli and many other cell cultures. For example, production of commercial pharmaceuticals such as recombinant insulin (Eli Lilly), erythropoietin (Amgen), and interferon (Roche) all involve fermentation as an essential step.

Rapid advances in biotechnology have enabled the development of high throughput alternatives to traditional laboratory bench top processes. Unfortunately, fermentation methods have not been amenable to automation because limits in current fermentation technology prevent the uninterrupted processing flow that characterizes automated high throughput systems. Existing fermentation systems typically involve multiple handling steps by either a batch processing method or a continuous processing method.

Current production scale batch processes involve first fermenting in large scale, bulk fermentation vessels, then processing the fermentation medium to isolate the desired fermentation product, followed by transferring this product into the production stream for further processing, and finally cleaning the fermentation apparatus for the next batch. In a large-scale batch culture, it is generally necessary to provide a high initial concentration of nutrients in order to sustain cell growth over an extended time. As a result, substrate inhibition may occur in the early stages of cell growth and then may be followed by a nutrient deficiency in the late stages of fermentation. These disadvantages result in sub-optimal cell growth rates and fermentation yields. Another disadvantage of this method lies in the need to individually dispense the fermentation products from the bulk fermentation apparatus into separate sample vessels for further processing. Thus, by producing the fermentation product on a bulk scale, the fermentation product is not immediately available for automated processing. Further disadvantages include the decreased efficiency of both transferring the material to another sample vessel, as well as cleaning and sterilizing the fermentation apparatus for the next batch. These disadvantages result in increased production costs, inefficient production times and decreased yields.

Continuous batch processes involve siphoning off the fermentation product from the bulk fermentation vessel and continuously adding nutrients to the fermentation medium according to a calculated exponential growth curve. This curve, however, is merely an approximation that does not accurately predict cell growth in large, industrial scale quantities of fermentation medium. Consequently, due to the unpredictable nature of large-scale fermentation environments, experienced personnel are required to monitor the feeding rate very closely. Changes in the fermentation environment may result in either poisoned fermentation products being siphoned off into the production stream or sub-optimal production yields due to starved fermentation mediums. As a further disadvantage, unpredictable fermentation product yields affect the accuracy of subsequent processing steps. For example, when the fermentation yield decreases, the amount of aspirating, the amount of reagent dispensed, or the centrifuge time is no longer optimized, or even predictable. Frequent or continuous monitoring of the fermentation process and adjustment of the fermentation conditions is often not practicable or efficient in a production scale process.

Fermentation remains a key-processing step in a number of industries, particularly in biotechnology industries, and thus a need exists for incorporating fermentation processes into current multiple process systems, such as automated high throughput systems. A process that produces a precise, known, and repeatable amount of unpoisoned fermentation product with limited human interaction or sample vessel transfer is essential to integrating fermentation into modem production processes.

Centrifugation, like fermentation, is a key technology in many fields and industries. It may be performed on a mass production scale or an experimental, bench top scale. For example, centrifuges are used in a wide variety of disciplines, including the chemical, agricultural, medical and biological fields. In particular, centrifuge technology is integral to chemical syntheses, cell separations, radioactive isotope analyses, blood analyses, assaying techniques, as well as many other scientific applications.

The recent identification of the more than 31,000 genes comprising the human genome highlights one important use of centrifuge technology, namely the determination of each gene's function, which has become of paramount biomedical importance. Because certain genes encode multiple proteins, it is estimated that as many as 1,000,000 proteins must be produced and isolated to understand completely the function of each gene in the human genome. Centrifugation is an important step in isolating and separating proteins, but protein isolation frequently requires several labor intensive and time-consuming sequential procedures that often involve more than one centrifugation step for each isolation process.

Particularly for commercial applications, these proteins and other products utilizing centrifuge technology must be synthesized analyzed or isolated on a production scale. Likewise, rapid advances in laboratory equipment have transitioned traditional laboratory bench top processes to more automated high-throughput systems. Unfortunately, limits in current centrifuge technology prevent the uninterrupted processing flow that characterizes automated high throughput systems.

These and other disadvantages are highlighted in a typical protein isolation process. Generally, a sample is centrifuged, removed from the centrifuge and a portion of the sample is removed, often by aspiration, from the sample at a separate processing station. At yet another processing station, a reagent is often dispensed into the remaining sample, followed by sonication in a separate sonication device (also at another processing station). Once the contents of the sample have been sonicated, the sample is placed back in the centrifuge and undergoes another centrifugation step. Frequently, this centrifugation-aspiration-dispensing-sonication-centrifugation cycle is repeated more than once for a particular protein isolation.

This cycle and all its drawbacks are also representative of many other applications involving centrifugation. Disadvantageously, typical sonication and centrifugation steps are not amenable to automated processing flows because of the need to physically transfer large numbers of samples to and from various processing stations. For example, in the example described above, a sample must be moved from a centrifugation station to an aspirating station, to a dispensing station, to a sonication station, and back to a centrifugation station. Unfortunately, this cycle may be repeated several times before a particular protein or other targeted material is isolated. Accordingly, the labor-intensive nature of the isolation process poses severe time constraints and cost increases, particularly when integration of the centrifuge step or the sonication step into an automated multiple process system is currently unavailable.

As centrifugation remains a key processing step in a number of industries, and particularly in biotechnology industries, a critical need exists for incorporating centrifugation processes into current multiple process systems such as automated high throughput systems. Developing a method and apparatus that reduces the need to transfer samples to a separate processing station for each processing step is essential to integrating centrifugation into modem production processes such as an automated high throughput system.

Accordingly, there is a need for a method and an apparatus that can perform multiple processing steps on a sample in a single vessel accurately and precisely while minimizing waste.

SUMMARY OF THE INVENTION

It is therefore an object of the present invention to provide a method and apparatus for performing multiple processing steps on a sample in a single vessel. It is a separate object of the present invention to minimize the time, cost, clean up and labor associated with conventional fermentation, centrifugation and other processing methods and devices.

The present invention alleviates to a great extent the disadvantages of the known methods and apparatus for performing processing steps such as fermentation and centrifugation on a sample. Accordingly, the present invention improves the accuracy and precision in performing multiple processing steps on a sample.

Briefly, the present invention provides a method and apparatus for performing multiple processing steps on a sample in a single vessel. Thus, for example, nutrients may be added to a sample in a vessel, the sample in the vessel may be fermented at one station, and the sample in the vessel may be placed in a centrifuge at a separate station without having to transfer the sample to another vessel.

Thus, in one aspect the present invention provides a method of processing a sample in a single vessel, the method comprising performing multiple automated processing steps on the sample in the vessel, wherein one of the automated processing steps is automated fermentation of the sample in the vessel. An automated processing step is performed entirely by a machine or at most with operator input through an operator interface. The automated processing steps may occur before, after or before and after the automated fermentation. The automated processing method is preferably performed in parallel on multiple samples.

Thus, the present invention provides a method comprising: performing a plurality of fermentations, each fermentation in a different sample vessel; and performing a further processing step on the plurality of fermented samples where each sample is retained in the same sample vessel during the fermentation and processing steps.

In a preferred embodiment the present invention is used in conjunction with the methods, devices and systems for fermentation described in U.S. patent application entitled "Multi-Sample Fermentor and Method of Using Same", serial number to be assigned, filed Feb. 8, 2001, which is incorporated herein by reference in its entirety. The present invention also preferably may be used in conjunction with the methods, devices and systems for centrifugation described in U.S. patent application entitled "Automated Centrifuge and Method Of Using Same", serial number to be assigned, filed Feb. 8, 2001, which is incorporated herein by reference in its entirety. The sample in a vessel may be moved, for example from a fermentor to a centrifuge, in a preferred embodiment by a robotic gripper as described in U.S. patent application entitled "Gripper Mechanism", serial number to be assigned, filed Feb. 26, 2001, which is incorporated herein by reference in its entirety.

In a preferred embodiment, a sample comprising organisms that express a particular protein to be produced is fermented, centrifuged and then several additional downstream processing steps may be performed, either in or out of the sample vessel in order to isolate and purify the protein. Once purified, the protein may be crystallized to form a crystallized protein. Once crystallized, crystals of the protein may be bombarded with x-rays in order to determine a 3-dimensional structure of the protein.

Certain companies, such as Syrrx, Inc. of San Diego, Calif., are making attempts to perform high throughput crystallizations. Such efforts require large numbers of different proteins to be recombinantly expressed and purified prior to crystallization. The present invention provides technology to make the production of a large number of different proteins via fermentation practical.

For example, Syrrx, Inc. is developing a process to crystallize tens to thousands of proteins per day; depending on the circumstances. Various numbers of different protein crystallizations may be performed per day, for example 100–900,000 protein crystallizations per day, 1,000–800,000 protein crystallizations per day, 10,000–700,000 protein crystallizations per day or 100,000–600,000 protein crystallizations per day. A robot may test each protein or protein variant and the same numerical ranges apply to how many proteins or variants may be tested by the robot. The crystallized proteins may then be analyzed on an imaging station. For example, the imaging station may analyze 100–1 million images, 1,000–900,000 images, 10,000–800,0000 images, or 100,000–700,000 images. The images are generated from protein crystal experiments that are formed each day, for example 100–140,000 crystal experiments per day, 1,000–100,000 crystal experiments per day, or 10,000–90,000 crystal experiments per day.

Advantages associated with the present invention include a reduced amount of time required to perform the multiple process steps on the sample. In addition, the present invention provides a reduced amount of clean up, disposal, and labor, thereby reducing the overall cost of operation. Another advantage realized by the present invention is an increased accuracy, thereby increasing the reliability of the results of the multiple process method.

One advantage of the present invention is that the sample vessels are capable of undergoing multiple process steps before, during or after fermentation. Each of these sample vessels has a gripping surface that a transporter uses to transfer the sample vessel to another processing station. These sample vessels are constructed such that post- and pre-fermentation steps may be conducted directly on the sample in the sample vessel. The compatibility of the sample vessel with other processing steps in the production eliminates increased production costs incurred both from first transferring fermentation product from a bulk fermentation vessel to a sample processing vessel, and then cleaning and sterilizing the bulk fermentation vessel. Further, eliminating a transfer step increases the efficiency of the overall process because of the decreased production time in not having to perform an extra transfer step and the increased yield from not losing any fermentation product in a transfer step.

Another advantage is that the fermentation apparatus may also be used in non-production scale environments where uninterrupted process flows are desirable. For example, the fermentation apparatus may be adapted to bench top processes on an experimental scale. This provides a further advantage of easily modifying the process later to an industrial scale by eliminating the step of redesigning the fermentation conditions that is usually required when scaling up a bench top process to a production scale process. Because the present invention utilizes smaller scale fermentation volumes, the unpredictability and unmanageability of bulk fermentation volumes is eliminated while still providing production scale quantities of fermentation product. A fermentation method or apparatus made according to the present invention may be utilized in any production, analysis, or system requiring multiple process steps.

Disadvantages resulting from increased production costs incurred from transferring fermentation product from a bulk fermentation vessel to a processing sample vessel are thus eliminated, as are the costs of cleaning and sterilizing a bulk fermentation apparatus for the next batch. According to the present invention, only the sample vessels will be cleaned at the end of the production process. In addition, valuable time is saved and yields are increased by not having to transfer a bulk fermentation product to a sample vessel that would be amenable to high throughput processing.

A further advantage is that calculation of exponential growth curves is more precise and reliable. This advantage is created because the fermentation volumes of the sample vessels are smaller than current production scale bulk fermentation systems. As a result, the nutrient feed may be more accurately optimized, resulting in the production of known and repeatable yields of fermentation product. In addition, each sample vessel may be equipped with sensors that transmit data to a controller, enabling the apparatus to respond to suboptimal fermentation conditions by appropriately adjusting environmental parameters. The present invention uses relatively small volumes by fermenting in a sample vessel and thereby eliminates the erratic fluctuations in environmental conditions that lead to unpredictability of fermentation growth yields. As a result, for example, the amount of aspirating, the amount of reagent dispensed, or the centrifuge time may now be predicted and optimized, leading to a more efficient and reliable system. The steps of monitoring of the fermentation process to determine the fermentation yield and monitoring or adjusting further processes downstream, such as dispensing or aspirating steps based on the amount of fermentation product, are eliminated when using smaller volume fermentation batches.

Another added advantage stems from the size of the fermentation batches. Because these fermentation batches are relatively small compared to the bulk fermentation vessels currently being used, known amounts of nutrients may be calculated to optimize the fermentation yield and known fermentation yields may be calculated on a predictable and repeatable basis. This reliability in calculating a fermentation yield enables the optimization of centrifuge times, dispensing accurate amounts of reagent, and aspirating accurate amounts of liquid that is otherwise not possible in current bulk fermentation systems. Without a reliable and repeatable fermentation product yield, it is very difficult to engineer a high throughput system involving many processing steps where each processing step, such as the amount dispensed or the time centrifuged, would otherwise vary according to a fluctuating fermentation yield. The present invention overcomes these difficulties by providing predictable and repeatable fermentation yields upon which to calculate and optimize subsequent processing steps, such as those used in a high throughput system.

These and other features and advantages of the present invention will be appreciated from review of the following detailed description of the invention, along with the accompanying figures in which like reference numerals refer to like parts throughout.

DETAILED DESCRIPTION OF THE INVENTION

The present invention relates methods and devices which allow for multiple different sample processing steps including a fermentation to be performed in the same sample vessel. The present invention also relates methods and devices which provide for some degree of automation for performing these different sample processing steps.

In one embodiment, a method is provided for fermenting a plurality of samples, comprising: providing a plurality of sample vessels each holding a fermentation sample in a sample carrier; fermenting the fermentation samples in the plurality of sample vessels in the carrier; and transporting the samples once fermented to a processing station where the samples may be further processed. Further processing may include, for example, centrifugation, sonication, and/or protein purification. Optionally, transporting the samples once fermented to a processing station is performed by transporting the samples in the same sample carrier as was used for the fermentation. This allows a series of samples to be fermented and then transported together.

In another embodiment, a method is provided for robotically moving an array of vessels to a fermentor, and then from a fermentor to a processing station. According to the method, a plurality of sample vessels are provided, each holding a fermentation sample. The plurality of sample vessels are introduced to a fermentation apparatus, preferably with the assistance of a robot. The fermentation samples are fermented and then transported once fermented with the assistance of a robot to a processing station where the samples are processed. In one particular application, processing station centrifuges the samples, most preferably in the same vessel as where the samples were fermented.

In another embodiment, a method is provided for robotically moving a same array of sample vessels from a fermentor to a centrifuge where samples are centrifuged in the same sample vessels. According to the embodiment, the method comprises fermenting a plurality of fermentation samples in a plurality of sample vessels; transporting the sample vessels containing the fermented fermentation samples to a centrifuge head with the assistance of a robot; and centrifuging the fermented fermentation samples in the same sample vessels in which the fermentation was performed. The method optionally further includes isolating the supernatant from the sample vessels after the fermentation samples have been centrifuged.

According to any of the above embodiments, the plurality of sample vessels preferably include at least 4 sample vessels, preferably at least 10 sample vessels, at least 20 sample vessels, and more preferably at least 40 sample vessels. Each sample vessel preferably contains at least 25 mL of fermentation sample, more preferably at least 50 mL of fermentation sample. Also according to any of the above embodiments, introducing the plurality of sample vessels to the fermentation apparatus may include moving at least 4 sample vessels at a time to the fermentation apparatus, more preferably moving at least 10 sample vessels at a time, and most preferably moving at least 20 sample vessels at a time. Also according to this embodiment, transporting the samples once fermented to a processing station may include transporting at least 4 sample vessels at a time from the fermentation apparatus to the processing station, more preferably moving at least 10 sample vessels at a time, and most preferably moving at least 20 sample vessels at a time.

Also according to any of the above embodiments, the plurality of sample vessels may have a layout which is maintained by the sample carrier, fermenting the fermentation samples including operably attaching the fermentor head relative to the sample vessels, the fermentor head having a layout which matches the layout of the sample vessels. Further according to any of the above embodiments, the fermentor head may have a plurality of probes which are inserted into the sample vessels when the fermentor head is operably attached to the sample vessels. Further according to any of the above embodiments, the plurality of probes may deliver oxygen to the sample vessels during the fermentation. The plurality of probes may also agitate the samples within the sample vessels during fermentation. When the fermentation is anaerobic, the plurality of probes may deliver inert gas to maintain anaerobic fermentation conditions in the vessels.

Also according to any of the above embodiments, the plurality of sample vessels may have a layout which is maintained by the sample carrier, fermenting the fermentation samples including operably attaching the fermentor head relative to the sample vessels, the fermentor head having a layout which matches the layout of the sample vessels. Further according to any of the above embodiments, the fermentor head may have a plurality of probes which are inserted into the sample vessels when the fermentor head is operably attached to the sample vessels. Further according to any of the above embodiments, the plurality of probes may deliver oxygen to the sample vessels during the fermentation. The plurality of probes may also agitate the samples within the sample vessels during fermentation. When the fermentation is anaerobic, the plurality of probes may deliver inert gas to maintain anaerobic fermentation conditions in the vessels.

Also according to any of the above embodiments, the plurality of sample vessels may be transported robotically to the processing station by robotic movement of the sample carrier. Alternatively the sample vessels may be transported manually.

Also according to any of the above embodiments, providing the plurality of sample vessels may include transporting to a fermentation station where the fermentation is performed with the assistance of a robot which moves the sample carrier to the fermentation station. Transporting the fermented samples may include moving the sample carrier with the assistance of a robot. According to this variation, the plurality of sample vessels may be transported robotically to the fermentation station and to the processing station without having to remove the sample vessels from the carrier.

The processing station to which the sample vessels are transported may include a centrifuge. The same sample vessels are preferably used to centrifuge the sample as are used to ferment the samples. Accordingly, the sample vessels are preferably compatible with being centrifuged.

If a sample carrier is used to transport the sample vessels, the method may further comprise removing the sample vessels from the sample carrier and introducing the same sample vessels into a centrifuge head compatible with the centrifuge. According to this variation, the sample vessels are preferably removed from the sample carrier and introduced into the centrifuge head with the assistance of a robot. Optionally, the sample carrier may be a centrifuge head compatible with the centrifuge.

The processing station may include an aspirator, the method further including aspirating the fermentation samples from the sample vessels. The sample carrier may be used to provide a layout to the plurality of sample vessels. The processing station may include an aspirator having an aspirator head having a layout which matches the layout of the sample vessels, the method further including operably attaching the aspirator head to the sample vessels and aspirating the fermentation samples within the sample vessels.

The processing station may include a dispenser, the method further including dispensing material into the fermentation samples. The sample carrier may be used to provide a layout to the plurality of sample vessels. The processing station may include a dispenser having a dispensing head having a layout which matches the layout of the sample vessels, the method further including operably attaching the dispenser head to the sample vessels and dispensing the fermentation samples within the sample vessels.

The layout which is maintained by the sample carrier may be a grid with at least 2 rows and at least 2 columns, optionally a grid with at least 4 rows and at least 2 columns, optionally a grid with at least 4 rows and at least 4 columns, and optionally a grid with at least 6 rows and at least 4 columns.

A robot is also provided for processing a plurality of fermentation samples, comprising: a robot having an arm and a griping element adjacent a distal end of the arm which is adapted to grip a plurality of sample vessels at the same time, the arm being capable of moving the griping element from adjacent a fermentor to adjacent a centrifuge head; and computer executable logic for controlling a motion of the robot arm and gripping element between the fermentor and the centrifuge head such that the robot moves a plurality of sample vessels from a fermentor into a centrifuge head at the same time. The robot is preferably capable of transporting at least 4 sample vessels at a time, more preferably moving at least 10 sample vessels at a time, more preferably moving at least 20 sample vessels at a time, and most preferably moving at least 40 sample vessels at a time.

The methods and devices of the present invention will now be described in greater detail.

II Sample Arrangement for Fermentation

Figure 1:
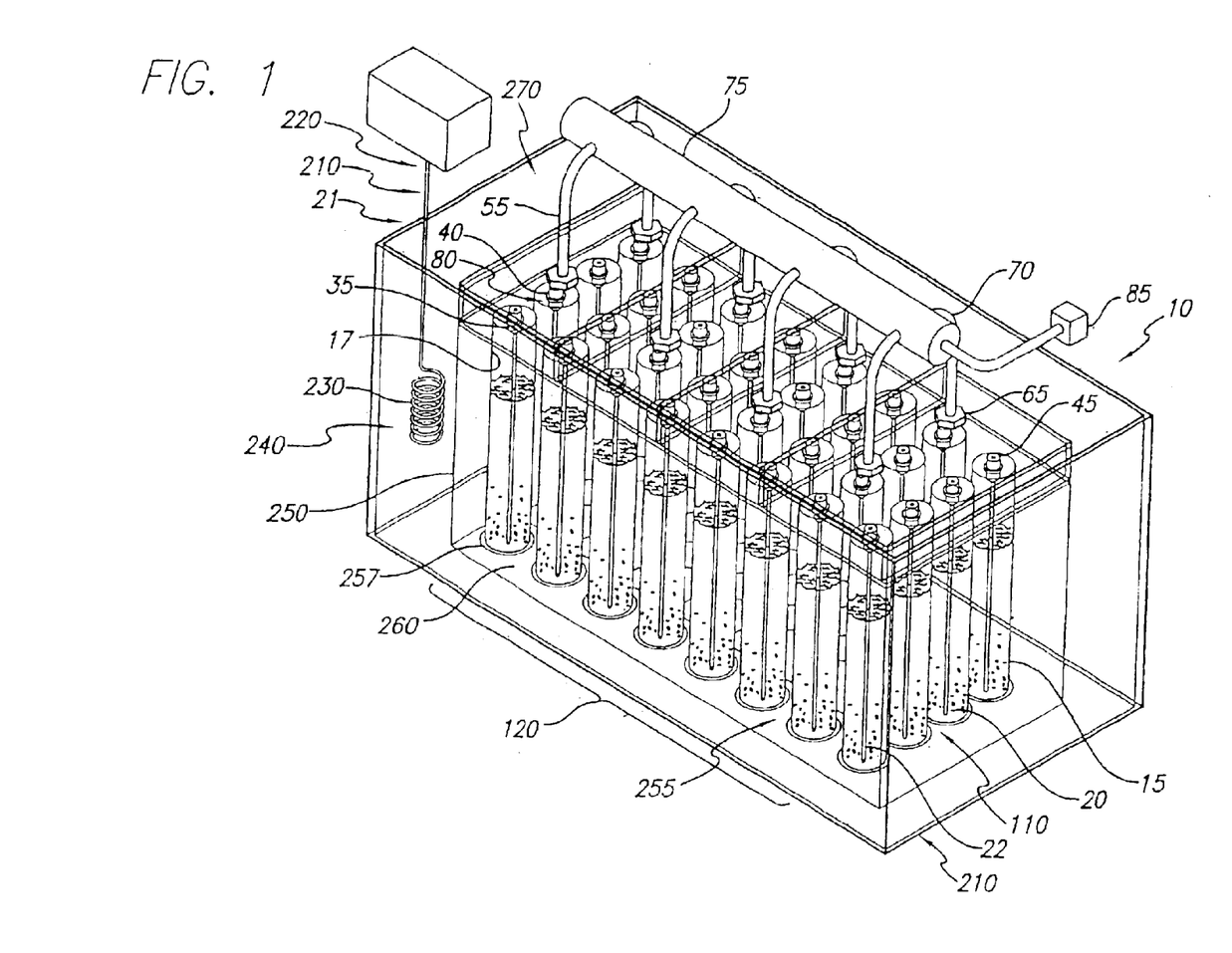
FIG. 1 is a perspective view of an apparatus in accordance with the present invention.

In FIG. 1, sample holder arrangement 255 is comprised of gripping surfaces 17, individual sample vessels 15, an array of sample vessels 110, a sample carrier 250, and an array of placement wells 260 corresponding to the array of sample vessels 110. Gripping surfaces 17 are located on each individual sample vessel 15, which collectively form sample vessel array 110. It is preferable that gripping surface 17 resides on the bottom of each sample vessel, but gripping surface 17 can be located on any surface of the sample vessel that enables sample vessel 15 to be transferred to or from another processing station or container frame 250.

In an embodiment shown in FIG. 1, individual sample vessels 15 are configured in a rectangular array 110, but the array may be configured in any physical construct that is conducive to fermentation or that is compatible with other processing steps. For example, a honeycomb, circular, triangular, or linear configuration may be more efficient in other contemplated applications of the present invention. The bottom of each individual sample well 15 is positioned within each placement well 257. The array of placement wells 260 preferably mirrors the configuration of the array of sample vessels 110 and is embedded in sample carrier 250. Placement wells may, however, be arranged in alternative configurations. For example, placement wells may be arranged as linear troughs, each holding a row of sample vessels. In another embodiment, placement wells are absent from sample carrier 250.

By using sample carrier 250, the entire array of sample vessels 110 may be transported to and from one fermentation processing station to another processing station in a multiple process production. In this illustrated example, sample carrier 250 transports array of sample vessels 110 into a temperature-controlled area 210 such as a water bath. In this embodiment, temperature controlled area 210 is comprised of water bath 240 in water bath container 215, which is controlled by water bath temperature controller 220 and temperature coil 230 immersed in water bath 240. Other forms of temperature control may be used, such as temperature controlled gel baths, ovens, glove boxes, or air chambers.

In one embodiment, colonization of bacteria and other preparative steps are performed within sample holder arrangement 255. For example, bacteria and initial nutrients are dispensed into each sample vessel 15 at a prior processing station. Being able to prepare bacteria directly in each individual sample vessel eliminates the need to inoculate a culture and initiate colonization in a separate container before transferring the sample to the fermentation apparatus. Using the sample holder arrangement of the present invention to colonize the fermenting bacteria decreases costs by eliminating a separate colonization arrangement. Once the bacteria are colonized, sample holder arrangement 255 is conveniently transported to water bath 240, or any other temperature controlled area 210.

II. Sample Vessels

Figure 2:
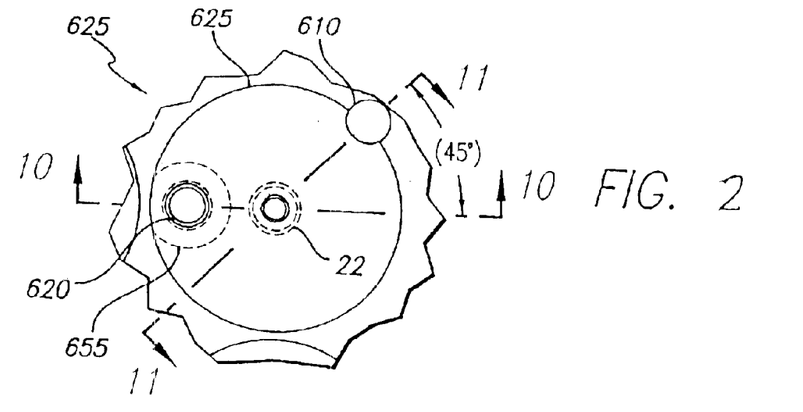
FIG. 2 is a bottom view of a sample vessel area of a dispensing plate in accordance with the present invention.
Figure 3:
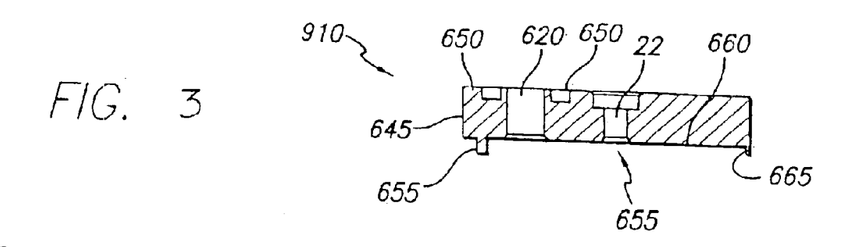
FIG. 3 is a cross sectional view of the sample vessel area shown in FIG. 2 taken along the line E—E in accordance with the present invention.
Figure 4:
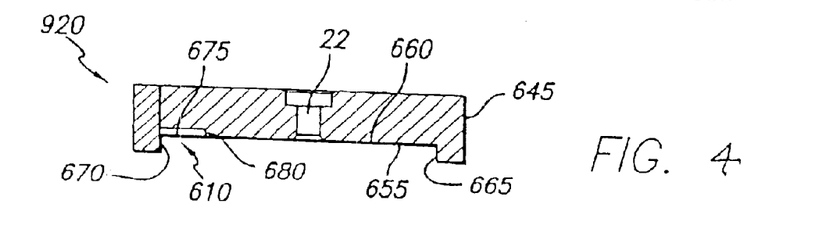
FIG. 4 is a cross sectional view of the sample vessel area shown in FIG. 2 taken along line F—F in accordance with the present invention.

In one embodiment, sample vessel areas 625, preferably located in bottom portion 646, correspond to array of sample vessels 110. FIGS. 2–4 illustrate features encompassed by sample vessel area 625 on bottom portion 646. In this preferred embodiment, cannula 22 is directly attached to bottom portion 646. Aperture 620 holds a dispensing tube 760 (not shown) for dispensing nutrients and other solutions into sample vessel 15. Aperture 620 can be used to access samples during the fermentation process. Pipettes or syringes can be used to draw samples or add nutrients, water, etc. Fastening groove 650 enables dispensing tube 760 to be fastened to dispensing plate 645. Indentation 655 and vertical edge 665 create a circular recess that helps immobilize sample vessel 15 within sample vessel area 625. Although in this embodiment, indentation 655 is circular and corresponds to the shape of sample vessel 655, other suitable shapes may be used.

Vent 610 is positioned on the circumference of sample vessel area 625 and allows gases and built up pressure to escape sample vessel 15. Referring to FIG. 4, vent 610 creates venting space 675. Because vertical edge 670 is larger than vertical edge 665, venting space 675 occupies a deeper recess than recess 655. The difference in height between vertical edges 670 and 665 is equal to the height of vertical edge 680 and determines the depth of venting space 675. Other configurations of venting space 675 and recess 655 (and, accordingly, vertical edges 665, 670, and 680) may be constructed such that built-up pressure within sample vessel 15 can escape through venting space 675 without contaminating other sample vessels.

When the top surface of sample vessel 15 abuts surface 660, gases, liquids, emulsions, or excess pressure built up in sample vessel 15 may escape through recess 655 and venting space 675. Cross-contamination of these escaping elements is significantly reduced because vertical edge 670 separates sample vessel 15 from an adjacent sample vessel 15. Moreover, gas flow from cannula 22 maintains a positive pressure within sample vessel 15 such that contaminants outside sample vessel 15 are not drawn in through venting space 675 into sample vessel 15 by way of recess 625. Other vents 610 may be configured such that excess gases, liquids, emulsions, or excess pressure may escape through vent 610 without cross-contaminating other sample vessels 15.

III. Vessel Surfaces and Composition

Figure 5:
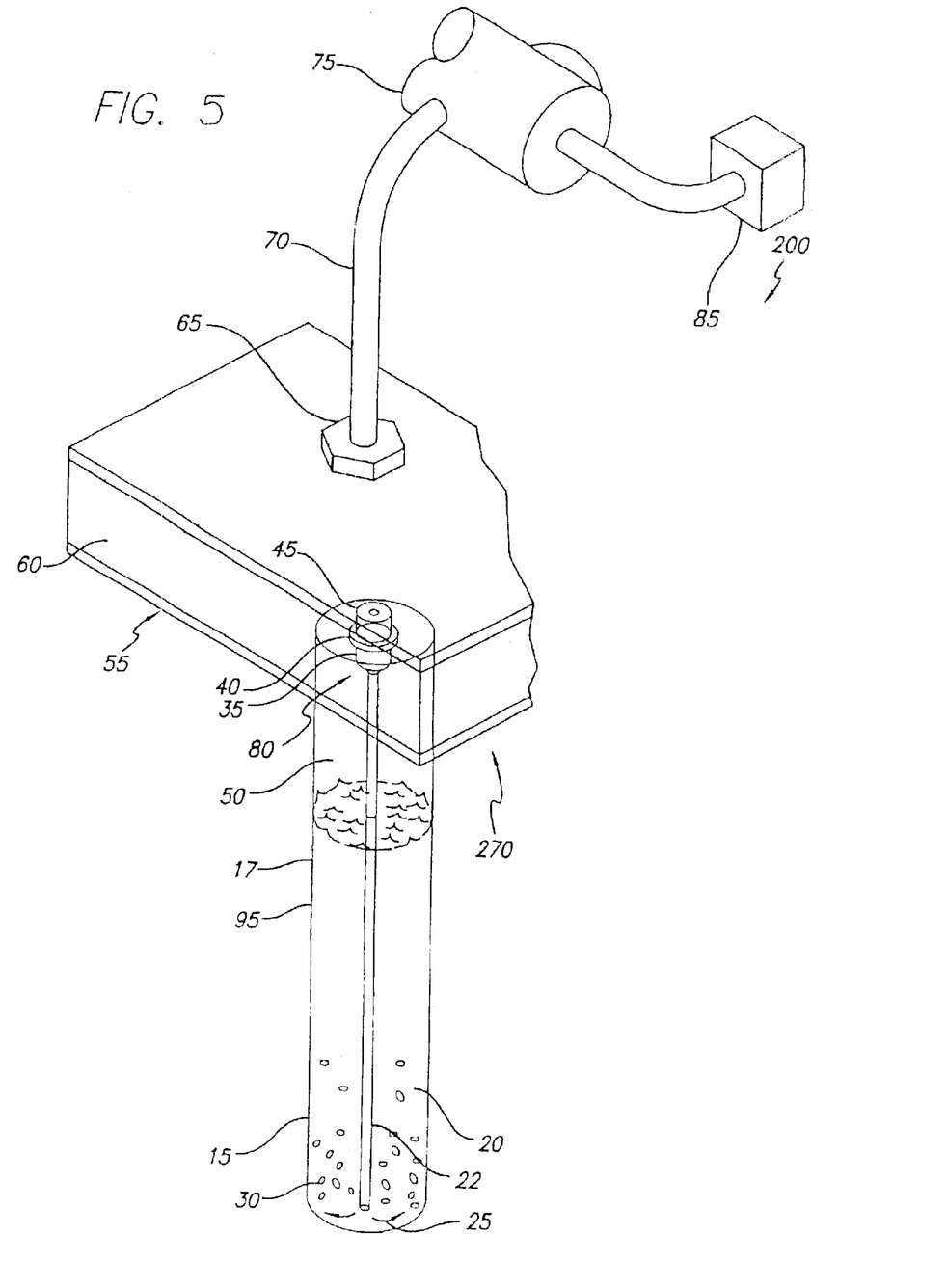
FIG. 5 is a perspective view of an individual sample vessel in accordance with the present invention.
Figure 6:
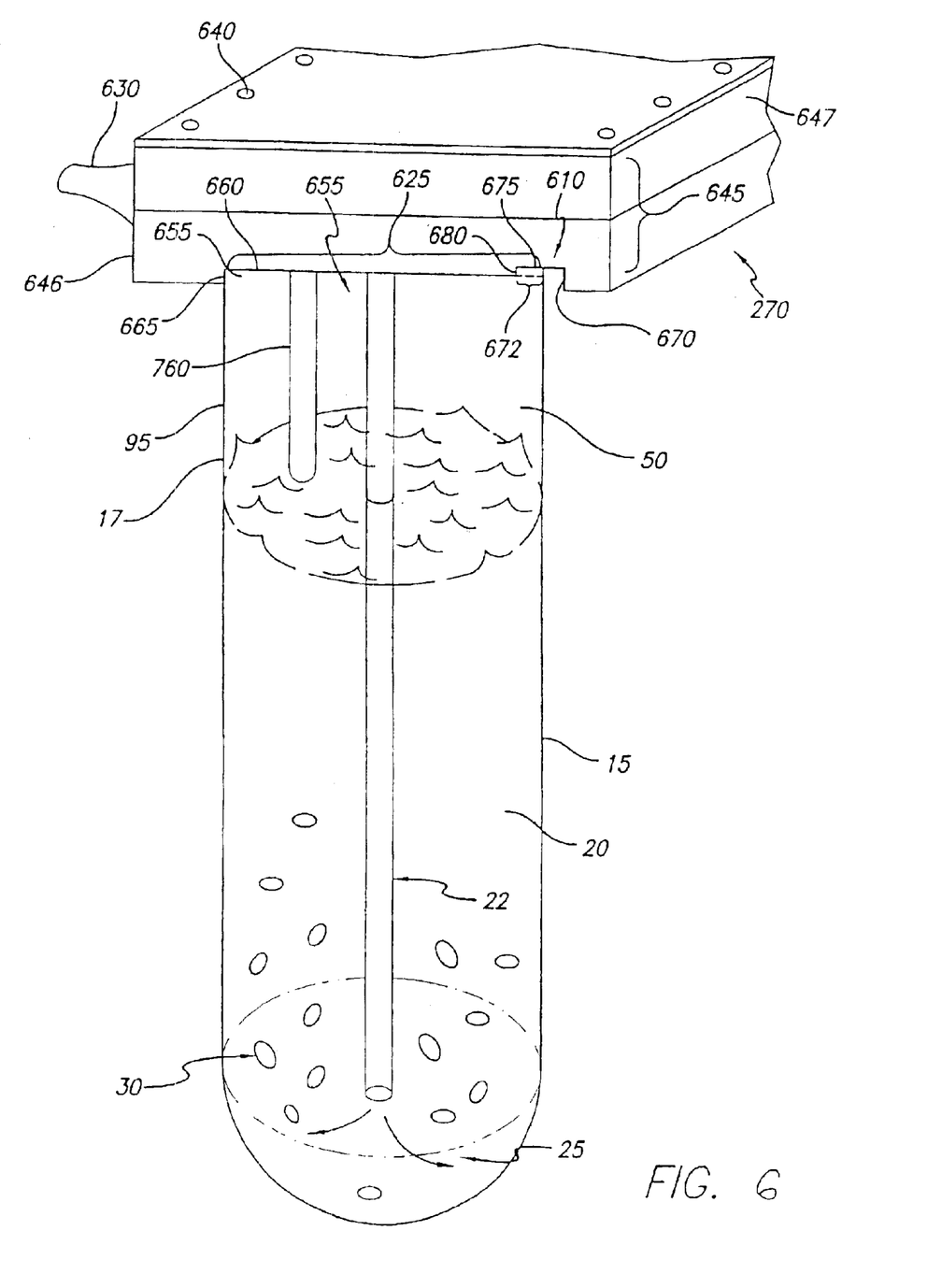
FIG. 6 is a perspective view of a sample vessel employing a dispensing plate in accordance with the present invention.

Referring to FIGS. 5 and 6, gripping surface 17 allows for automated or manual transfer of sample vessel 15 to and from the fermentation apparatus or another processing station. In one embodiment, gripping surface 17 is magnetic such that a magnet attracts gripping surface 17 and transfers the sample vessel to another processing station. In another embodiment, a gripping mechanism grips the outer sides of the sample vessel to effect transfer. In yet another embodiment, gripping surface 17 is a lip at the top of the sample vessel. Other surfaces that may be gripped in order to transport the sample vessel to or from the fermentation processing station are within the scope of the present invention. For example, gripping surface 17 may be on the inside, outside, top or bottom of sample vessel 15.

In a particular embodiment, individual sample vessel 15 is constructed of Pyrex glass, but other suitable materials may be used to construct sample vessel 15. For example, plastic, ceramic, aluminum, or any other material may be used that is non-reactive to fermentation medium 20 or to other materials involved in additional processes contemplated in a multiple process production, such as in a high throughput system. It will further be appreciated that fermentation medium 20 may be the same medium in each individual sample vessel 15 or, alternatively, array of sample vessels 110 may include a combination of different fermentation mediums. For example, fermentation medium 20 may be the same in each individual sample vessel 15 and contain the same fermentation broth for a bulk synthetic process. Alternatively, each fermentation medium 20 in array 110 may have a slightly different fermentation broth in order to optimize the production yield of a certain component.

IV. Vessel Top Surface and Post-Fermentation Transfer

In the illustrated example, a top surface of individual sample vessel 15 abuts directly onto surface 660 within sample vessel area 625. The top surface of sample vessel 15 is positioned within recess 655. Surface 660 preferably is not in contact with the entire circumference of the top surface of sample vessel 15. Also preferably, vent 610 is positioned adjacent to surface 660 such that a gap 672 exists between surface 660 and the vertical edge of sample vessel 15, thereby creating a passage for excess gases, emulsions, or pressure to escape from sample vessel 15 through venting space 675. Gas flow through cannula 22 provides sufficient pressure such that contaminants are not drawn into sample vessel 15 through venting space 675.

When fermentation is complete, sample carrier 250 transports array of sample vessels 110 from water bath 240, or any other temperature controlled area 210, to the next processing station. For example, sample carrier 250 may either manually or automatically transport array 110 to a centrifuge processing station. In one embodiment, the centrifuge processing station includes a centrifuge and a surface to hold container frame 250. Individual sample vessels, collectively, in groups, or singly, may be transferred from the container frame to the centrifuge by manipulating gripping surface 17. This may be done manually or by a robot which moves one or more sample vessels at a time to the processing station. Further processing steps may be conducted directly on the sample contained in each individual sample vessel 15 without transferring the sample out of sample vessel 15.

V. Method of Using Vessel to Ferment a Sample

Figure 7:
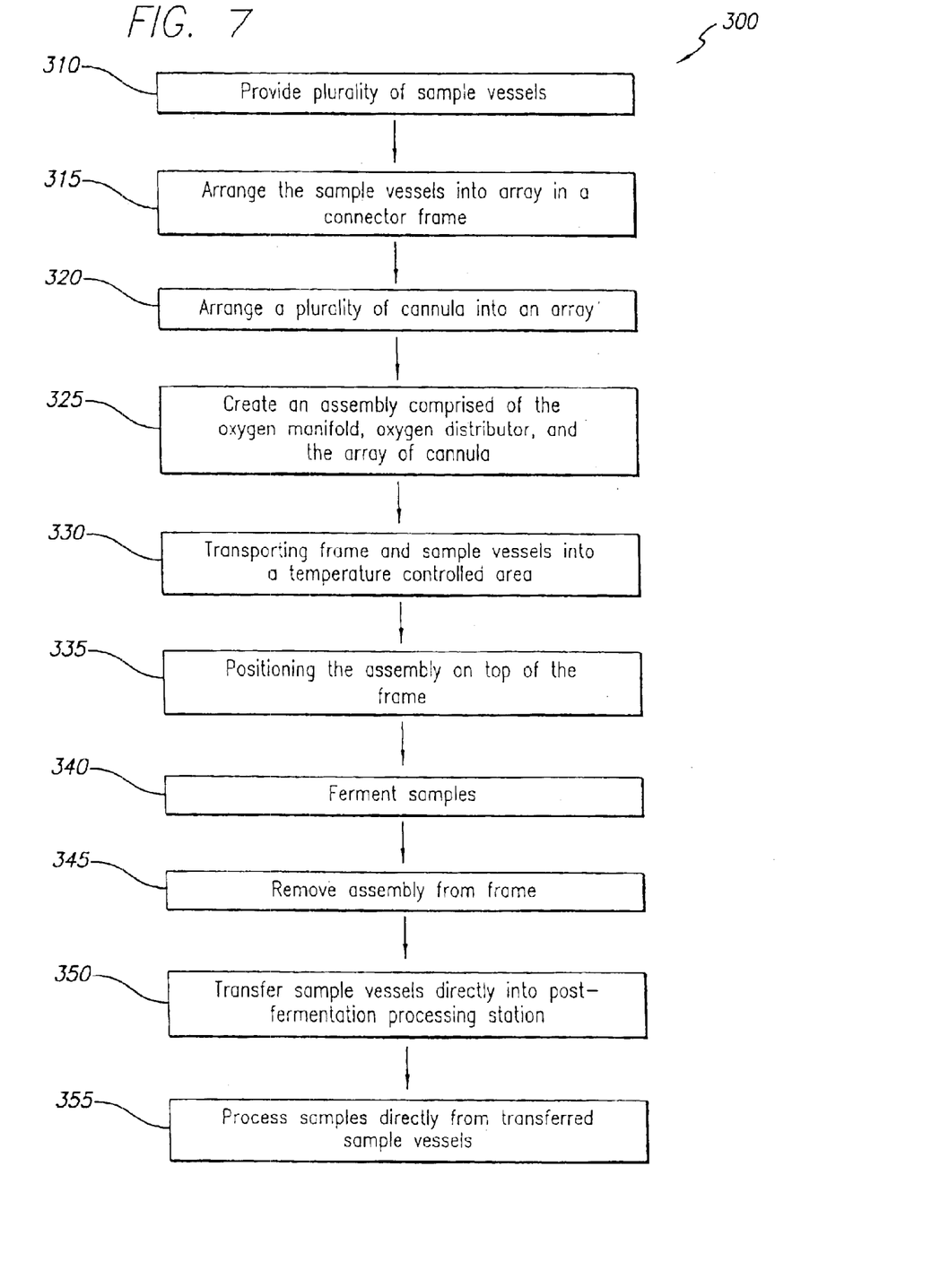
FIG. 7 is a block diagram of a method in accordance with the present invention.

In FIG. 7, block 315 arranges sample vessels 15 into an array 110. Array 110 may be configured in any shape that is practicable for the fermentation apparatus. For example, sample vessels 15 may be arranged in a rectangular array, a honeycomb configuration, or a linear array.

Block 330 transports container frame 250 containing sample vessels 15 to a temperature controlled area 210. Other methods used to control temperature know in the art are also contemplated within the present invention. For example, container frame 250 may be transported to a heated gel bath or a controlled temperature room used to maintain a constant temperature.

Block 335 positions gas distribution arrangement 270 created in block 330 on top of container frame 250. From this configuration, the array of sample vessels is fermented in block 340.

Once fermentation is complete, block 345 removes gas distribution arrangement 270 from container frame 250. Sample vessels 15 are transferred from container frame 250 directly to a post-fermentation processing station in block 350 by manipulating a gripping surface 17 located on each sample vessel. This post-fermentation processing station includes any processing step where the fermentation product may be processed directly from the sample vessel. For example, array of sample vessels 120 may be transferred, either manually or robotically, from the container frame directly to an automated centrifuge. Alternatively, sample vessels 15 may be transferred to an aspirating station or detecting station.

In block 350, the fermentation product in sample vessels 15 are directly transferred into a post-fermentation processing station and in block 355 the fermentation product is directly processed in the sample vessels themselves. For example, in one embodiment, sample vessels 15 are transferred directly to a centrifuge station in which sample vessels 15 are positioned directly inside the centrifuge such that sample vessels 15 act as centrifugation tubes and the fermentation product is centrifuged according to methods known in the art. Further processing steps such as aspirating reagent dispensing, or detecting may also occur directly in the sample vessel used in the fermentation process. In this way, the fermentation vessel provides a sample vessel that holds the sample throughout the entire production process, thereby eliminating excess waste from transferring sample material from sample vessel to sample vessel as well as decreasing the cost of washing and sterilizing a fermentation apparatus in addition to sample vessels from each production process step. Other multiple process productions or analyses may also be practiced in accordance with the present invention.

VI. Overall Method of Using the Sample Vessel

Figure 8:
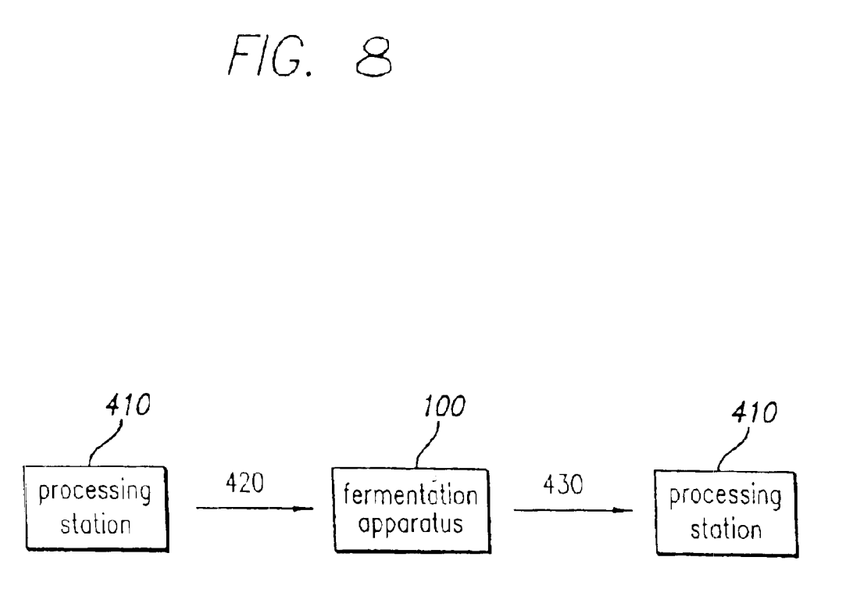
FIG. 8 is a block diagram showing a multiple process procedure in accordance with the present invention.

In FIG. 8, a block diagram 400 is shown wherein the present invention is integrated into a multiple step, multiple process production. Block 410 depicts a processing station prior to fermentation. In one embodiment, fermentation broth and fermentation nutrients are added to sample vessels 15 at prior processing station 410. Other processing steps involved in a multiple step production or analysis are also contemplated in accordance with the present invention. For example, bacteria colonization may occur in sample vessels 15 at a prior processing station 410. A transporter 420 transfers the sample vessel from processing station 410 to a fermentation apparatus such as fermentation apparatus 10. Other embodiments of a fermentation apparatus practiced in accordance with this invention may also be used. For example, fermentation apparatus 700 may also be used.

It will further be appreciated that transporter 420 may transfer the sample vessels individually, in groups, or in an array configured for the fermentation apparatus. For example, in one embodiment, container frame 250 transports the sample vessel array 110 to fermentation apparatus 10. Similarly, transporter 430 transports sample vessels 15 from a fermentation apparatus to a post-fermentation processing station 410. In one embodiment, transporter 430 transports container frame 250 holding array of sample vessels 110 to a centrifuge processing station 410. Post-processing station 410 may also be any other processing step occurring in a multiple process or analysis, such as an aspirating step, a dispensing step, or a detecting step. In this manner, multiple processing steps may be executed on a sample contained in the same sample vessel, thus enabling fermentation processes to be incorporated into high throughput or other multiple process systems.

VII. Preferred Centrifugation, Fermentation and Gripper Devices and Methods

The present invention alleviates to a great extent the deficiencies of known centrifugation processes by providing an automated centrifuge system that incorporates several processing steps within a single processing station. Briefly, the automated centrifuge system includes at least one centrifuge rotor defining a cavity. One or more movable sample vessels are structured to be insertable into the cavity. A transport is configured to position and insert one or more movable sample vessels into the cavity. Once the sample vessels are inserted into the cavity, the system performs a fluid-movement function such as aspiration, dispensing, or sonication.

One embodiment of the automated centrifuge system employs a centrifuge rotor defining a cluster of rotor apertures (also referred to as "holes") located in the rotor. Each aperture has a longitudinal axis and the longitudinal axes of the cluster of rotor holes preferably are substantially parallel, although any arrangement of rotor holes may be used that can suitably receive and position sample vessels. A group of movable sample vessels are positioned by a transport so that the movable sample vessels are capable of being inserted into the cluster of rotor apertures.

The automated centrifuge system of the present invention affords several advantages. For example, the rotor cavities are grouped in sets with each cavity in the set being substantially parallel to all the other cavities in the set. Such an arrangement permits the simultaneous insertion of a group of tubes for further processing steps such as automated aspiration or dispensing of fluids without removing the sample vessels to a separate processing station. In addition, a sonication device can also be inserted simultaneously with the aspiration/dispensing tube. Advantageously, suspended materials can be centrifuged, aspirated, sonicated, and centrifuged again without the removal of the sample vessels from the centrifuge and without human intervention. The present invention introduces numerous advantages over current technology in that multiple-step procedures involving centrifugation that formerly required substantial human involvement and physical transfer of sample vessels to separate processing stations are now incorporated into an apparatus that performs multiple step processes at a single processing station.

Moreover, the automated centrifuge system of the present invention increases the reproducibility of experimental results, thereby decreasing the possibility of operator variation or error. Accordingly, other advantages of the present invention include reducing operator error and increasing the consistency and reliability of experimental results.

In one aspect the present invention provides an automated centrifuge system. The system includes: (a) a group of movable tubes, each tube structured to transport a liquid; (b) a cluster of rotor holes located in a rotor, the cluster of rotor holes arranged to receive the group of movable tubes; and (c) a transport holding the movable tubes and constructed to substantially simultaneously move the group of tubes into the cluster of rotor holes.

The automated centrifuge system may include: (a) a rotor; (b) a cavity located in the rotor; (c) a tube structured to be insertable into the cavity; (d) a transport coupled to the tube; and (e) a controller communicating with the transport, the controller directing the transport to insert the tube into the cavity. Alternatively, the automated centrifuge system includes: (a) a cluster of holes located in a rotor; (b) a group of tubes configured to be received into the cluster of holes; (c) a transport operably coupled to the group of tubes; and (d) a controller that directs the transport to insert the group of tubes into the cluster of holes. The system may also include: (1) a second rotor, the second rotor including a cluster of holes; and (2) a movable platform coupled to the transport; wherein the movable platform moves the transport to selectively position the group of tubes for insertion into the cluster of holes in the rotor and into the cluster of holes in the second rotor.

In another aspect, the automated centrifuge includes: (a) means for placing a plurality of vessels in a plurality of centrifuge rotor cavities; (b) means for substantially isolating a majority of a component located in each vessel by centrifugation; (c) means for re-suspending a majority of the component in a first group of vessels; and (d) means for substantially simultaneously dispensing a substance into a second group of vessels.

In still another aspect, the invention provides a method of automated centrifugation. The method includes the steps of: (a) placing a vessel in a centrifuge rotor cavity; (b) substantially isolating a majority of a component located in the vessel by centrifugation; and (c) re-suspending a majority of the component while the vessel is located in the centrifuge rotor cavity. In another aspect the method of automated centrifugation includes the steps of: (a) arranging a cluster of cavities on a centrifuge rotor, each cavity configured to receive a sample; (b) inserting a set of elongated tubes into the cluster of cavities, each tube being inserted into a corresponding cavity for depositing a liquid in each cavity; and (c) centrifuging the liquid and the sample.

The inventions also features a centrifuge rotor. The rotor includes a cluster of holes located in the centrifuge rotor, each hole including a longitudinal axis. The longitudinal axes of the cluster of holes are substantially parallel.

Other aspects of the invention feature: (a) automated loading and unloading of the centrifuge rotor using a robot; (b) automated manipulation of samples in vessels in a centrifuge rotor using a robot; (c) an automated method for moving samples into cavities of a centrifuge rotor using a robot; (d) an automated method for manipulating samples in vessels in a centrifuge rotor using a robot; (e) controller logic (i.e., the logic for controlling the various automated operations of the system, as well as the sample tracking logic); and (f) an overall automated method.

The number of various elements or steps of the invention may be modified. For example, in preferred embodiments, the rotor body may comprise 1, 2, 3, 4, 5, 6, 7, 8 or any whole number of clusters and each cluster may have 1, 2, 3, 4, 5, 6, 7, 8, 9, 10, 11, 12, 13, 14, 15, 16 or any whole number of cavities. The number of cavities or clusters can thus be, for example, any integer between 1 and 100, preferably between 1 and 50 and more preferably between 1 and 25. In addition, the robot is capable of positioning at least 2 centrifuge vessels, for example, into cavities in a same cluster of the centrifuge rotor at the same time. Again, any number of centrifuge vessels can be positioned by the robot in such a manner, preferably the number is any integer between 1 and 100, more preferably between 1 and 50 and most preferably between 1 and 25. Finally, the plurality of probes are capable of performing a function on at least 3 different samples, for example, at the same time. The probes, however, may be able to perform a function on at least any number of different sample at the same time, preferably the number of different samples is any integer between 1 and 100, more preferably between 1 and 50 and most preferably between 1 and 25.

The systems, devices and methods of the present invention preferably may also include means or steps for recognizing specific tubes or vessels, or groups of tubes or vessels, as they are placed into the centrifuge and/or me or steps for indexing or tracking one or more tubes or vessels as they are transferred from the centrifuge to another system, device or method, for example a fermentor. For example, the system, device or method may incorporate barcodes or colors to achieve the above, either manually or robotically.

The present invention greatly alleviates the disadvantages of known fermentation systems by providing a fermentation apparatus that may be incorporated into high throughput processing systems.

Briefly, the fermentation apparatus is constructed to produce a known and repeatable amount of unpoisoned fermentation product using multiple fermentation vessels. To facilitate further processing and to be compatible with other product processing steps, the fermentation apparatus preferably has an array of sample vessels arranged in a container frame. The container frame may be configured to hold the sample vessels during fermentation and to transport the vessel array to or from another processing station.

The sample vessels may be arranged in the container frame in an array format to facilitate tracking of the sample vessels during the production process and to make the format of sample vessels compatible with other processing steps. In a preferred embodiment, a total of 96 sample vessels are arranged in an 8×12 format. An arrayed 96-member sample format is compatible with other methods for sample handling such as a 96-well microtiter plate. An 8×12 arrayed format is similarly compatible with sample handling formats designed for greater numbers of sample vessels, such as 384- and 1536-member sample formats, which are multiples of the 96-member sample format.

In a preferred embodiment a cannula array, having a number of cannula corresponding to the number of sample vessels in the sample vessel array, is configured such that each cannula may be placed inside a sample vessel. The cannula array may be attached to a gas distributor that delivers gases from a gas source through the cannula into the sample vessel. Depending on the gas delivered, either aerobic fermentation with agitation or oxygenation or anaerobic fermentation, i.e., with a nitrogen bubbler, for example, can be performed with the present invention. Because the fermentation volume for each individual sample vessel is smaller than a bulk fermentation apparatus, the fermentation product yields are more predictable and cell growth rates are more effectively optimized.

In one aspect the present invention features a method of fermenting a plurality of samples. The method involves the steps of processing a plurality of samples contained in associated sample vessels and fermenting the plurality of samples in the sample vessels. The processing can be done before and/or after the fermenting and the steps preferably are performed at different locations. Each sample preferably is a relatively small, non-bulk volume of material.

An important aspect of the present invention is that a plurality of samples being fermented in associated sample vessels will have similar yields and growth rates. Thus, the plurality of samples may be monitored and harvested at approximately the same, which minimizes the need for human intervention and which produces more predictable fermentation results.

In a preferred embodiment, the method involves the steps of: (a) providing a plurality of sample vessels, each sample vessel having a gripping surface and holding an associated fermentation sample; (b) transporting the plurality of sample vessels to a fermentation apparatus; (c) fermenting each fermentation sample by delivering oxygen, nitrogen or another gas capable of fermenting the sample from a gas source into each sample vessel; (d) manipulating each gripping surface located on each sample vessel; and (e) transferring the sample vessels from the fermentation apparatus to a processing station, wherein processing occurs within the sample vessels. The method may also include the steps of: (1) arranging the sample vessels into an array; (2) arranging a plurality of cannula into a corresponding array such that each cannula may be inserted into an associated corresponding sample vessel; (3) coupling the cannula array to a gas arrangement; and (4) positioning the gas arrangement such that each cannula is inserted into its associated corresponding sample vessel.

In another aspect, the invention provides a multiple process, multiple sample fermentation apparatus. The apparatus includes a means for processing a plurality of samples contained in associated sample vessels and a means for fermenting the plurality of samples in the sample vessels. The apparatus preferably also includes a process controller.

In a preferred embodiment, the apparatus includes: (a) a fermentation processing station, constructed to receive an array of sample vessels; (b) an array of sample vessels, each sample vessel containing a sample, wherein each sample vessel is capable of undergoing multiple process steps before, during or after fermentation; (c) a gas arrangement positioned to provide oxygen, nitrogen or any other gas capable of fermenting the sample to each sample in the array of sample vessels; (d) a cannula array, configured such that each cannula is attached to the gas arrangement and positionable inside a sample vessel; and (e) a gripping surface on the sample vessel such that a transporter using the gripping surface can transfer the sample vessel from the fermentation processing station to another processing station, wherein the sample is processed directly from the sample vessel. The apparatus may also include: (1) a dispenser, positioned such that feed solution is dispensed within each sample vessel; (2) a sensor with a sample within the sample vessel; and (3) a process controller, configured such that the sensor and the dispenser are in communication with the controller.

Other aspects of the invention feature: (a) methods of moving an array of vessels to a fermentor, and then from a fermentor to a processing station with the assistance of a sample carrier; (b) methods of robotically moving an array of vessels to a fermentor, and then from a fermentor to a processing station; (c) methods of robotically moving a same array of sample vessels from a fermentor to a centrifuge where samples are centrifuged in the same sample vessels; (d) and a fermentor head apparatus.

In preferred embodiments, the fermentations are in sync in the sense that they are roughly growing at the same rate. This allows them to get harvested at the same time. This may be achieved, for example, by use of a negatively regulated promoter. Also, in another preferred embodiment, a certain media plus bubbler increases the amount of soluble protein produced. In yet another preferred embodiment, as noted above, a total of 96 sample vessels are arranged in an 8×12 format or a 384- or 1536-member sample formats is used.

One advantage of the present invention is that the sample vessels are capable of undergoing multiple process steps before, during or after fermentation. Each of these sample vessels has a gripping surface that a transporter uses to transfer the sample vessel to another processing station. These sample vessels are constructed such that post- and pre-fermentation steps may be conducted directly on the sample in the sample vessel. The compatibility of the sample vessel with other processing steps in the production eliminates increased production costs incurred both from first transferring fermentation product from a bulk fermentation vessel to a sample processing vessel, and then cleaning and sterilizing the bulk fermentation vessel. Further, eliminating a transfer step increases the efficiency of the overall process because of the decreased production time in not having to perform an extra transfer step and the increased yield from not losing any fermentation product in a transfer step.

Another advantage is that the fermentation apparatus may also be used in non-production scale environments where uninterrupted process flows are desirable. For example, the fermentation apparatus may be adapted to bench top processes on an experimental scale. This provides a further advantage of easily modifying the process later to an industrial scale by eliminating the step of redesigning the fermentation conditions that is usually required when scaling up a bench top process to a production scale process. Because the present invention utilizes smaller scale fermentation volumes, the unpredictability and unmanageability of bulk fermentation volumes is eliminated while still providing production scale quantities of fermentation product. A fermentation method or apparatus made according to the present invention may be utilized in any production, analysis, or system requiring multiple process steps.

Disadvantages resulting from increased production costs incurred from transferring fermentation product from a bulk fermentation vessel to a processing sample vessel are thus eliminated, as are the costs of cleaning and sterilizing a bulk fermentation apparatus for the next batch. According to the present invention, only the sample vessels will be cleaned at the end of the production process. In addition, valuable time is saved and yields are increased by not having to transfer a bulk fermentation product to a sample vessel that would be amenable to high throughput processing.

A further advantage is that calculation of exponential growth curves is more precise and reliable. This advantage is created because the fermentation volumes of the sample vessels are smaller than current production scale bulk fermentation systems. As a result, the nutrient feed may be more accurately optimized, resulting in the production of known and repeatable yields of fermentation product. In addition, each sample vessel may be equipped with sensors that transmit data to a controller, enabling the apparatus to respond to suboptimal fermentation conditions by appropriately adjusting environmental parameters. The present invention uses relatively small volumes by fermenting in a sample vessel and thereby eliminates the erratic fluctuations in environmental conditions that lead to unpredictability of fermentation growth yields. As a result, for example, the amount of aspirating, the amount of reagent dispensed, or the centrifuge time may now be predicted and optimized, leading to a more efficient and reliable system. The steps of monitoring of the fermentation process to determine the fermentation yield and monitoring or adjusting further processes downstream, such as dispensing or aspirating steps based on the amount of fermentation product, are eliminated when using smaller volume fermentation batches.

Another added advantage stems from the size of the fermentation batches. Because these fermentation batches are relatively small compared to the bulk fermentation vessels currently being used, known amounts of nutrients may be calculated to optimize the fermentation yield and known fermentation yields may be calculated on a predictable and repeatable basis. This reliability in calculating a fermentation yield enables the optimization of centrifuge times, dispensing accurate amounts of reagent, and aspirating accurate amounts of liquid that is otherwise not possible in current bulk fermentation systems. Without a reliable and repeatable fermentation product yield, it is very difficult to engineer a high throughput system involving many processing steps where each processing step, such as the amount dispensed or the time centrifuged, would otherwise vary according to a fluctuating fermentation yield. The present invention overcomes these difficulties by providing predictable and repeatable fermentation yields upon which to calculate and optimize subsequent processing steps, such as those used in a high throughput system.

In order to overcome the deficiencies with known, conventional robotic devices, a robotic gripping mechanism is provided. Briefly, the gripper mechanism includes a first arm having a first pivotable member and a second arm also having a second pivotable member, with the second arm moveably coupled to the first arm. The first and second pivotable members are structured to grasp an object therebetween. In an alternative embodiment, the pivotable members are removed, and the first and second arms are pivotable so that the edges of an object, such as a sample plate, contacts the first and second arms.

The robotic gripper mechanism according to the invention provides an accurate, extremely precise automated system for grasping, moving and positioning objects. The gripper mechanism accomplishes the accurate positioning of objects by positively locating the grasped object in all three translational coordinate axes. For example, one method employed by the present invention comprises grasping the object with two arms that include pivot members. During the grasping process, the x-axis, or side-to-side position of the object is determined. The z-axis, or vertical position of the object is also determined during the grasping process. Finally, the object is then pushed against a surface to determine a y-axis, or fore-and-aft position the object.

The gripping mechanism of the present invention affords its users with a number of distinct advantages. First, unlike prior robotic grippers, the present gripping mechanism accurately determines the three translational axes of an object with extreme accuracy. Moreover, the determination of the position of the object is performed quickly, thereby enabling high throughput processing of a large quantity of objects.

In one aspect, the present invention features a robotic gripper apparatus. The gripper apparatus includes a grasping mechanism coupled to a controller. The grasping mechanism includes a first arm and a second arm. The gripper apparatus determines the position of an object in all three translational coordinate axes with an accuracy of about 0.1 millimeters in each direction and the gripper apparatus also grasps the object.

In a preferred embodiment the robotic gripper apparatus includes: (a) a first arm including a first pivotable member; and (b) a second arm including a second pivotable member, the second arm moveably coupled to the first arm; wherein the first and second pivotable members are structured to grasp the object therebetween.

In another aspect, the invention provides a robotic gripper apparatus for grasping an object that includes: (a) means for providing first and second arms; (b) means for grasping the object with the first and second arms; and (c) means for pushing the object against a surface to position the object relative to the first and second arms.

In yet another aspect, the invention features a method of grasping an object. The method involves the steps of using a robotic gripper apparatus to determine all three translational coordinate axes of the object with an accuracy of about 0.1 millimeters in each direction and of using the robotic gripper apparatus to grasp the object. The gripper apparatus includes a grasping mechanism coupled to a controller, and the grasping mechanism includes a first arm and a second arm.

In a preferred embodiment, the method involves the steps of: (a) providing first and second arms; (b) grasping the object with the first and second arms; and (c) pushing the object against a surface to position the object relative to the first and second arms.

Finally, another aspect of the invention provides a method of moving an object. The method involves the steps of: (a) approaching the object with a robotic gripper apparatus; (b) grasping the object with the gripper apparatus; (c) removing the object from an initial position with the gripper apparatus; (d) pressing the object against a push surface with the gripper apparatus; and (e) placing the object in a new position with the gripper apparatus.

Figure 9:
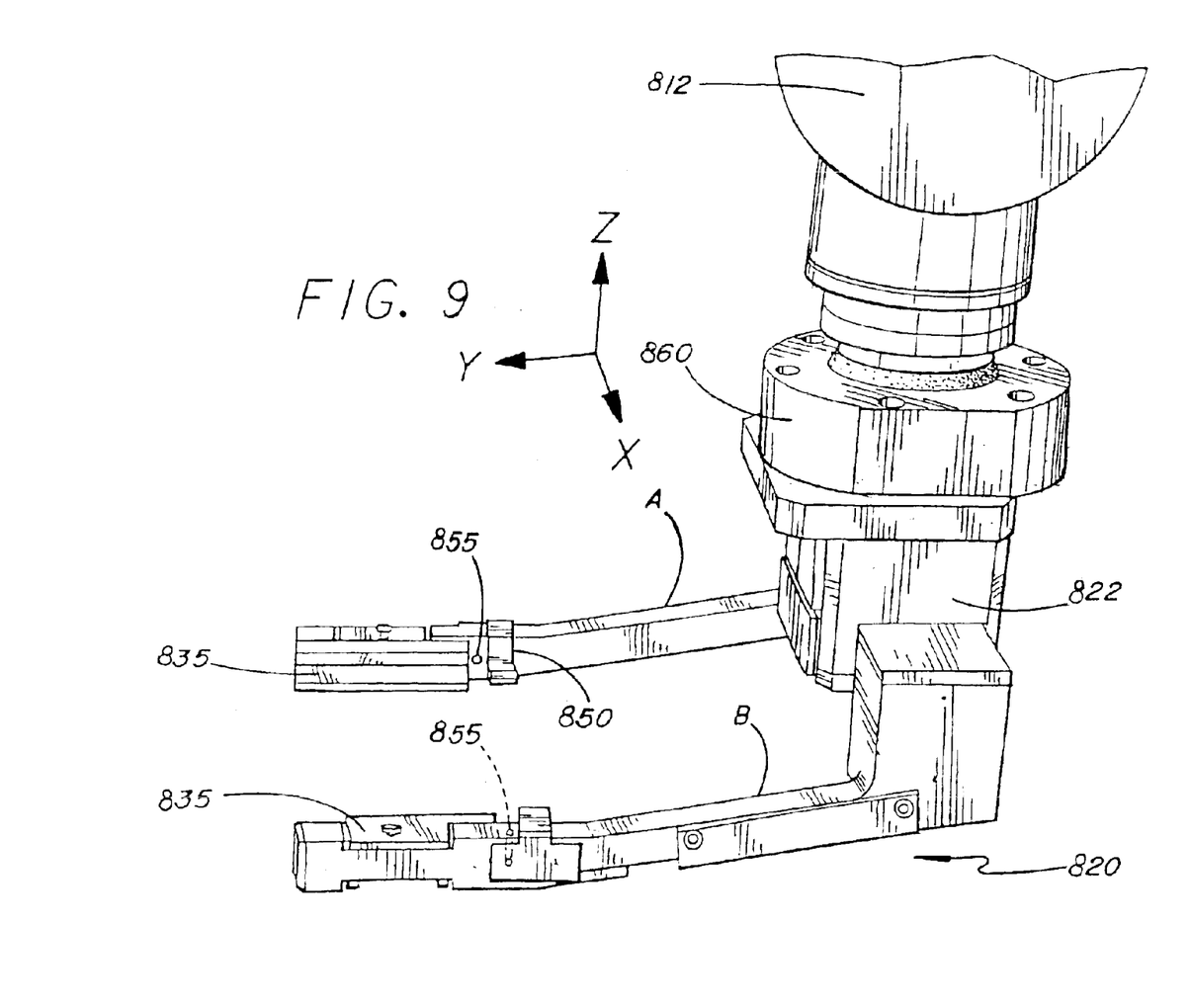
FIG. 9 is a perspective view of the gripper mechanism constructed according to one embodiment of the present invention.

Referring to FIG. 9, the grasping mechanism 820 of the gripper apparatus is illustrated. Grasping arm A and grasping arm B extend from gripper mechanism body 822. The body 822 is connected to a breakaway 860 that is deflectably coupled to the boom 812. The breakaway is structured to detect angular, rotational and compressive forces encountered by the grasping mechanism 820. The breakaway acts a collision protection device that greatly reduces the possibility of damage to components within the work perimeter by the accidental impact of the grasping mechanism 820 or grasping arms A and B with objects. For example, when the grasping mechanism 820 impacts an object, the breakaway 860 will deflect, thereby also causing the grasping mechanism 820 to deflect. When the controller 815 detects the deflection, it stops movement of the robotic gripper mechanism. In a preferred embodiment, the breakaway is a "quick-stop" collision sensor manufactured by Applied Robotics of Glenville, N.Y., U.S.A. The breakaway 860 is a dynamically variable collision sensor that operates on an air pressure system. Other types of impact detecting devices could be employed and they can be operated hydraulically, magnetically, or by other means known in the art.

Body 822 connects the grasping arms A and B to the breakaway 860. When directed by the controller 815, the body 822 moves the grasping arms A and B, away from or toward each other, to grasp and release objects. In a preferred embodiment, the body 822 is a gripper manufactured by Robohand of Monroe, Conn., U.S.A. In a preferred embodiment, the gripper is pneumatically driven, but other means for operating the gripper can be employed, such as magnetics and hydraulics.

Referring to FIG. 9, grasping arms A and B extend from the body 822 and include pivot members 835. Positioned adjacent to the pivot members 835 are sensors 855 and stops 850. The sensors 855 communicate with the controller 815 and determine the location of objects adjacent to the arms A and B. In a preferred embodiment, the sensors 855 are optical sensors, but photoelectric, infrared, magnetic, or other suitable sensors can be employed.

Figure 10:
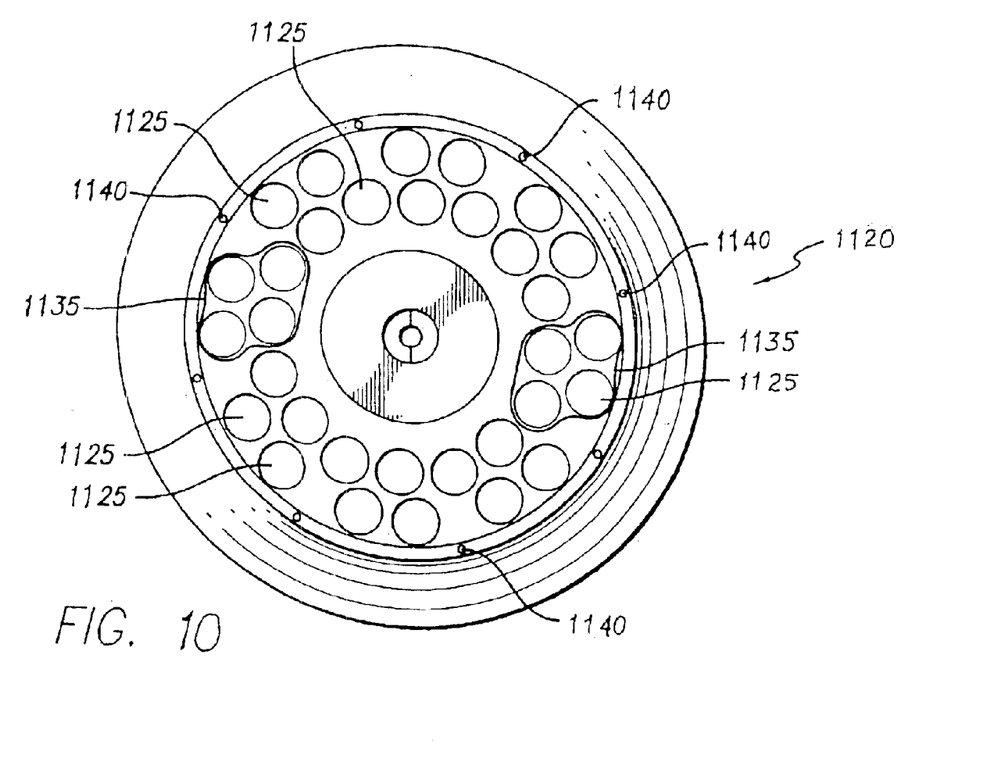
FIG. 10 is a plan view of a centrifuge rotor constructed according to the present invention and a group of sample vessels inserted therein.
Figure 10A:
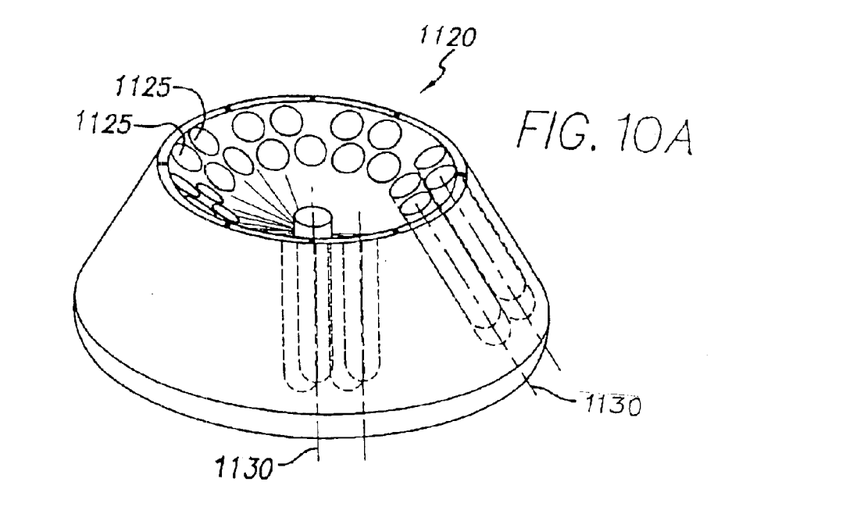
FIG. 10A is a phantom view of the embodiment illustrated in FIG. 10.

Referring to FIGS. 10 and 10A, another aspect of the present invention is illustrated. A centrifuge rotor 1120 for use in a centrifuge system contains a plurality of cavities 1125, or rotor holes. Although in the preferred embodiment the cavity 1125 is a rotor hole, the cavity may take other forms. For example, the cavity may be a well in a sample plate. Each cavity 1125 has a longitudinal axis 1130 and is configured to receive a vessel (not shown). In the preferred embodiment, the vessel holds a biological sample. However, the biological sample, or any other sample, may be placed directly in the cavity to satisfy application specific needs.

As shown in FIGS. 10 and 10A, the rotor holes are arranged in clusters 1135. In the embodiment illustrated, the cluster 1135 comprises four cavities 1125. The longitudinal axis 1130 of each cavity 1125 in each cluster 1135 are substantially parallel. The clusters 1135 can be arranged substantially radially in the centrifuge rotor 1120, as shown in FIGS. 10 and 10A. In contrast to conventional centrifuge rotors that have individual rotor holes with non-parallel longitudinal axis, the rotor 1120 of the present invention arranges clusters 1135 where the cavities are substantially parallel in a cluster and it is only the clusters 1135 that are radially arranged on the rotor. The number of cavities 1125 in each cluster 1135 can vary depending upon the size of the rotor 1120 and the size of the cavities 1125. The number of clusters 1135 in each rotor 1120 can also vary. For example, a preferred embodiment centrifuge rotor 1120 has 32 cavities 1125 arranged in eight clusters 1135. Another embodiment has 96 cavities 1125 arranged in 24 clusters 1135.

As illustrated in FIGS. 10 and 10A, the shape of the rotor 1120 is substantially triangular with a flat base and an annular upper surface. The rotor 1120 can be made from aluminum, steel, plastics or other suitable materials. A preferred embodiment is manufactured from aluminum alloy and coated with an epoxy-teflon mixture that resists reaction with laboratory chemicals. However, the material, size and general shape of the rotor may be adjusted for application specific needs.

Each cavity 1125 of the centrifuge rotor 1120 is sized to accommodate a vessel. The vessel typically is a test tube. Other vessels may be substituted. For example, the vessel may be a well in a plate, with the plate having a plurality of sample wells. In such a manner the plate could be received in the rotor. The vessels are capable of undergoing multiple process steps before or after the isolation process. Each of these vessels has a surface that a transporter could use to transfer the vessel to another processing station. These vessels are constructed such that post- and pre-isolation steps may be conducted directly on the material in the vessel. The compatibility of the vessel with other processing steps performed prior to or after the isolation process eliminates increased production costs incurred from transferring material from one vessel to a second or third vessel, and then cleaning and sterilizing the used vessels. Further, eliminating one or more transfer steps increases the efficiency of the overall process because of the decreased production time in not having to perform an extra transfer step and the increased yield from not losing any material in a transfer step.

The most common use for a centrifuge is to concentrate or purify materials that are in suspension or dissolved in fluids. The fluid is placed in the vessel with the vessel then placed in the cavity 1125. The rotor 1120 is then spun by a rotor motor 1127 or other suitable device to create a centrifugal force on the fluid inside in the vessel. The centrifugal force acts on the objects inside the fluid separating them by their different densities. For example, suspended particles denser than the suspending liquid tend to migrate towards the side of the vessel. When the centrifugation process is complete a pellet of the denser material has formed on the side, or bottom of the vessel. Illustrated in FIGS. 10, and 10A, the cavities 1125 are angled relative to the rotor rotational axis. Vessel located in the cavity 1125 is thereby also angled, which positions the pellet near the bottom of the vessel. In a preferred embodiment, this angle is about 32 degrees, but other angles can be employed to locate the pellet in a different location in vessel.

One skilled in the art will appreciate that the present invention can be practiced by other than the preferred embodiments which are presented in this description for purposes of illustration and not of limitation, and the present invention is limited only by the claims that follow. It is noted that equivalents for the particular embodiments discussed in this description may practice the invention as well.

What is claimed is:

1. A method comprising:
   performing a plurality of fermentations, each fermentation in a different sample vessel; and performing a further processing step on the plurality of fermented samples where the sample is retained in the same sample vessel as the fermentation during the processing step.

2. The method of claim 1, wherein the further processing step is centrifugation of the fermented samples in the sample vessels in which the fermentations were performed.

3. The method of claim 1, further comprising grasping the sample vessels with a robotic gripper apparatus in order to move the sample vessels from a first location where the fermentations are performed to a second location where the further processing step is performed.

4. The method of claim 1, wherein the fermentations comprise fermentations of prokaryotic or eukaryotic cells, or viral particles.

5. The method of claim 1, wherein the fermentation is an anaerobic fermentation.

6. The method of claim 1, wherein the fermentation is a bacterial fermentation where a recombinant protein is expressed.

7. The method of claim 6, wherein the method further comprises isolating recombinant proteins expressed during the fermentations after the further processing step.

8. The method of claim 7, wherein the recombinant proteins are isolated by column chromatography.

9. The method of claim 7, wherein the method further comprises crystallizing the isolated recombinant proteins.

10. The method of claim 9, wherein the method includes crystallizing tens to thousands of proteins per day.

11. The method of claim 9, wherein the crystallized proteins are used to design drugs.

12. The method of claim 9, wherein structures of the crystallized proteins are analyzed by X-ray crystallography.

13. The method of claim 12, wherein the protein structures are used in computer assisted drug design.

14. The method of claim 1, wherein the further processing step uses a robot that tests tens to thousands of variants of a protein.

15. The method of claim 14, wherein the robot includes a plate handler that carries plates from one station to another.

16. The method of claim 1, wherein the samples comprise a prokaryotic, eukaryotic, or viral expression system comprising a gene fragment or variant in a vector.

17. The method of claim 1, wherein performing a plurality of fermentations includes performing at least 96 fermentations at the same time.

18. The method of claim 1, wherein hundreds of fermentations are performed per day using the method.

19. The method of claim 10, further comprising analyzing on an imaging station, more than one million images from thousands of crystallizations.

20. The method of claim 10, further comprising identifying crystals from the crystallizations, using crystal-detecting algorithms.

21. The method of claim 10, further comprising using a robot to mount and center about 30 to about 50 crystals per hour with the robot.

* * * * *